United States Patent [19]

Abitbol

[11] 4,157,710
[45] Jun. 12, 1979

[54] ABDOMINAL ELECTRODE FOR FETAL MONITORING

[76] Inventor: Moise M. Abitbol, 41 Allenwood Rd., Great Neck, N.Y. 11023

[21] Appl. No.: 877,019

[22] Filed: Feb. 13, 1978

[51] Int. Cl.$^2$ .............................................. A61B 5/04
[52] U.S. Cl. ..................... 128/642; 128/698
[58] Field of Search ............. 128/2.06 E, 2.1 E, 404, 128/418, DIG. 4, 347, 350 R

[56] References Cited

U.S. PATENT DOCUMENTS

| | | | |
|---|---|---|---|
| 3,042,041 | 7/1962 | Jascalevich | 128/350 R |
| 3,313,293 | 4/1967 | Chesebrough et al. | 128/2.1 E |
| 3,580,240 | 5/1971 | Cosentino | 128/2.06 E |
| 3,580,242 | 5/1971 | La Croix | 128/2.06 E |
| 3,750,650 | 8/1973 | Ruttgers | 128/2.06 E |
| 3,856,020 | 12/1974 | Kovac | 128/347 |

*Primary Examiner*—William E. Kamm

[57] ABSTRACT

An electrode for introduction through the abdominal wall of a pregnant woman or animal for monitoring the fetal heart is described which includes an elongated rod having at one end a handle for rotating the rod about its longitudinal axis, and a helical electrode tip portion at the other end of the rod which is pointed to penetrate through the abdominal wall as the rod is rotated. The rod is designed with a length sufficient to extend through the abdominal section and uterine wall as the rod is rotated such that the electrode tip portion will hook onto the fetus skin and thereby pick up the fetus cardiogram. A flexible plastic shroud is attached near the electrode handle and encircles the electrode rod with adhesive means on one end of the shroud for securing to the abdominal skin around the area where the electrode enters the abdomen. The plastic shroud prevents foreign particles and germs from entering the opening while the electrode is in place, thereby maintaining a sterile environment. After fetal monitoring, an electrode jack connector is unplugged from the back of the electrode handle, the rod and electrode tip portion backed off from the fetus by reverse rotation, and the shroud removed.

11 Claims, 3 Drawing Figures

ABDOMINAL ELECTRODE FOR FETAL MONITORING

BACKGROUND OF THE INVENTION

The present invention relates to electrodes for monitoring of the fetal heart, and more particularly to an electrode which is introduced through the abdominal wall of the mother and hooked onto the fetus.

DESCRIPTION OF THE PRIOR ART

Modern monitoring equipment allows today a careful surveillance of the fetal heart while the fetus is still inside of the womb. The main technical difficulty has been how to implant the electrodes on the skin of the fetus for the purpose of picking up the electric impulses coming from the fetal heart, so that they may be transmitted to a recording equipment. The known devices presented in the prior art employ an insulated wire or rod which is introduced into the body of the mother and, at the end of the insulated wire, a hook or other cutting penetrating means is adapted to be implanted in the skin of the fetus. The fetal penetrating means can be a fishhook as disclosed by LaCroix in U.S. Pat. No. 3,580,242, or a mounted coil as disclosed in U.S. Pat. No. 3,472,234 to Tachik. Two common fetal electrodes used today are the double spiral electrode described by Ruttgers in U.S. Pat. No. 3,750,650 and the single spiral electrode as described by Hon in U.S. Pat. No. 3,827,428. Both of these electrodes must be introduced through the vagina in order to be implanted on the fetal scalp.

The prior art electrodes require that the fetal head be accessible to the examining fingers of one hand through the vagina. Then, the device is introduced by the other hand through the vagina and then through the dilated cervix. The amniotic membranes are ruptured either spontaneously or artificially. An Ellis clamp, or a plastic guiding tube, or a plastic driving tube, are used to introduce and/or implant the tip of the electrode on the fetal scalp.

The disadvantages of the above described prior art fetal electrodes are as follows:

(1) Their use is restricted to patients in a state of advanced labor as it requires the uterine cervix to be moderately dilated and the amniotic membranes to be ruptured. If the membranes are not ruptured and if the cervix is not at least 2 to 3 cm. dilated, the implantation of the electrode is very difficult, if not impossible. Often, there is need to study the fetal heart in women not in labor and the known devices are inappropriate for that purpose.

(2) The introduction of the electrode is rather difficult in women having their first baby, especially in the earliest stage of labor, because the vagina is rather narrow as it has not been dilated by a previous vaginal delivery.

(3) Removal of the electrode is difficult unless the labor has moved to a more advanced stage where the head of the fetus has descended further down in the birth canal and the uterine cervix is much further dilated; this is so because the guiding tubes of the known devices cannot be introduced to perform the implanting operation in the reverse order.

(4) Another disadvantage of the known devices is that because of their bulkiness and the need of human hands for their implantation on the fetal head, they cannot be used on experimental animals. Experimental studies in pregnant animals are fundamental today since many of these studies cannot be done on human beings. Most of the experimental pregnant animals used today are of much smaller size than humans, and their amniotic membranes rarely rupture during labor. Today, in order to study fetal heart in pregnant animals, one had to open the abdomen of the mother animal and open the pregnant uterus of the animal so as to implant the electrodes on the fetal skin. Thus there is an urgent need for an electrode to be used in pregnant animals without resorting to extensive operations.

(5) With the use of known devices, there is the possibility of infection to the fetus being introduced by the electrodes through the fetal scalp. For example, this problem is disclosed in "Neonatal Scalp Abscess and Fetal Monitoring" in the American Journal of Obstetrics and Gynecology, Vol. 129, page 187, Sept. 1977. Also the continuing motion of the fetal head produced by uterine contractions exposes the small incision made on the fetal scalp by the electrode to infections from germs present in the vagina.

(6) The known devices are limited to implantation of the electrode on the fetal scalp. This can be dangerous as it can cause intracranial hemorrhage and even brain damage.

SUMMARY OF THE INVENTION

It is an object of the present invention to provide an electrode for fetal monitoring which can be placed on the fetal body both before or during labor. It is another object to provide an electrode for fetal monitoring which is not inserted through the uterine cervix area and, therefore, does not require such cervix to be opened in order to provide fetal monitoring. It is another object to provide an electrode for fetal monitoring which can be easily removed from its operative position. It is another object to provide an electrode for fetal monitoring which can also be used on animals.

It is another object of the present invention to provide an electrode for fetal monitoring which maintains sanitary conditions in the working area and thereby avoids infections.

It is a further object of the present invention to provide an electrode for fetal monitoring which can be implanted on select portions of the fetal both other than the scalp, such as, the hip or shoulder, and thereby avoid contact with sensitive organs, such as, the scalp and underlying brain so that no intracranial hemorrhage or brain damage can occur.

These and other objectives are achieved by the present invention which provides ane electrode for introduction through the abdominal wall of a pregnant woman or animal for monitoring the fetal heart is described which includes an elongated rod having at one end a handle for rotating the rod about its longitudinal axis, and a helical electrode tip portion at the other end of the rod which is pointed to penetrate through the abdominal wall as the rod is rotated. The rod is designed with a length sufficient to extend through the abdominal section and uterine wall as the rod is rotated such that the electrode tip portion will hook into the fetus skin and thereby pick up the fetus cardiogram. A flexible plastic shroud is attached near the electrode handle and encircles the electrode rod with adhesive means on one end of the shroud for securing to the abdominal skin around the area where the electrode enters the abdomen. The plastic shroud prevents foreign particles and germs from entering the opening while the electrode is in place, thereby maintaining a sterile environment. After fetal monitoring, an electrode jack connector is unplugged from the back of the electrode handle, the rod and electrode tip portion backed off from the fetus by reverse rotation, and the shroud removed.

DESCRIPTION OF THE PREFERRED EMBODIMENTS

Figure 1:
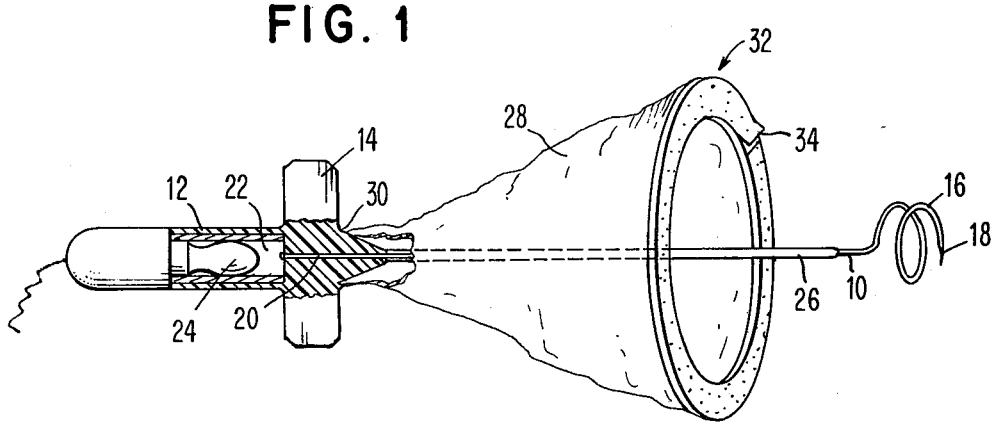
FIG. 1 is a side view of the electrode device illustrative of the present invention.

Referring to FIG. 1 there is shown a side view of the electrode device illustrative of the present invention. The device includes an elongated rod 10 attached to or forming a part of a handle at one end 12, such handle 12 having a pair of wing portions 14 to facilitate grasping and rotation of the electrode. The other end of the rod 10 is connected to a helical electrode tip portion 16 having a sharp pointed end 18 for penetrating through the abdominal section of a pregnant woman or animal, as will be described. Electrical pickup of the fetal cardiogram passes as a signal from the tip portion 16, through the rod 10 which interconnects via its end portion 20 with a female connector 22. A mating connector 24 carries the signal via conventional means to signal application and recording equipment, not shown. Rod 10 is covered with an insulator material 26 to prevent pickup of a noise as well as cardiogram signals of the mother.

A flexible plastic shroud 28 is attached at one end 30 to the handle 12 and encircles the rod 10 as a sterile, protective covering around the rod 10 and tip 16 area, as will be described. The open end of the shroud toward the electrode tip portion 16 is provided with a circumferential ring 32 coated with an adhesive material adapted to stick onto the abdominal skin around the opening through which the rod 10 passes, as will be described and shown in FIG. 2. The ring 32 of adhesive material may be of the pressure-sensitive type with a protective removable strip 34.

Figure 1A:
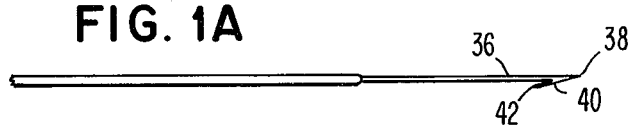
FIG. 1A shows an alternate form of electrode tip comprising a straight tip portion with a sharp pointed end and cutting edge.

Referring to FIG. 1A, there is shown an alternate form of an electrode tip which is comprised of a straight tip portion 36 with a sharp, pointed end 38 and a cutting edge 40. The back of the cutting edge 40 has a small hook portion 42 for holding the tip in place on the fetus skin. The electrode tip shown in the embodiment of FIG. 1A is inserted through the abdominal wall of the pregnant woman or animal by applying direct pressure against the tip to cause a puncturing and cutting action, as opposed to the screw type action of the helical type shown in the FIG. 1 embodiment.

Figure 2:
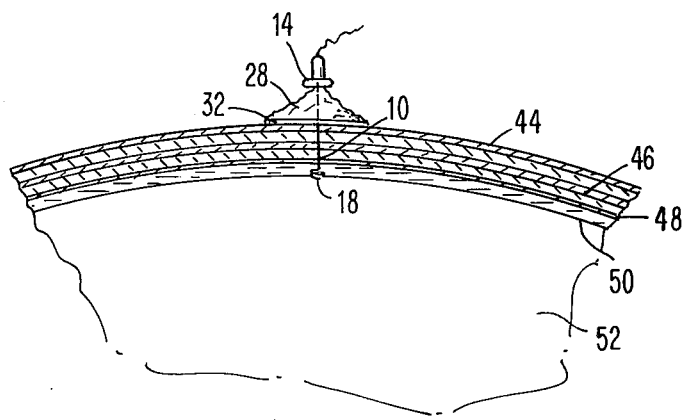
FIG. 2 shows the electrode of FIG. 1 in its operative position on the abdominal wall of a pregnant woman and attached to the fetus skin.

Referring to FIG. 2, there is shown the electrode device of FIG. 1 in its operative position through the abdominal wall of a pregnant woman. Here, the abdominal section of the woman is represented by the abdominal skin 44, covering a layer of fat tissue, muscle tissue 46 and the uterine wall 48. The skin 44 of the mother is prepared in a sterile manner in the area where the electrode device will be implanted. The electrode rod 10 extends through the abdominal section with the electrode end 18 extending through the uterine wall 48 and hooked on to the skin of the fetus 50. The plastic shroud 28 encircles the electrode rod 10 with the adhesive ring 32 attached to the skin 44 around the rod 10. As an example, since the abdominal wall of a woman has a thickness of about 1 to 1½" depending on the thickness of the fat layer and muscle tissue, the electrode rod 10 is about 3" long to insure that the tip 18 end reaches the fetus 50. It is noted that conventional medical practice during delivery or prior to delivery enables a doctor to determine where the fetus head is located in the abdomen. This will insure that the electrode tip is inserted at a location in the abdominal wall which is away from the head, thereby avoiding the possibility of intracranial hemorrhage or brain damage casued by the tip.

It is noted that the rod 10 and rod 36 shown in FIGS. 1 and 1A, respectively, can be made hollow and adapted with conventional fluid injection means, not shown, at the end portion 20 such that medication can be injected through the hollow rods 10 and 36 and their respective tips 18 and 38, into the fetus.

Thus, the device of the present invention provides for fetal monitoring on humans and animals via the abdomen, thereby avoiding the problems and dangers associated with fetal monitors requiring insertion through the uterine cervix area. Also the subject device, with its protective shroud, maintains sanitary conditions in the working area on the abdomen. In this connection, it should be understood that the shroud 28 need not be permanently attached to the device but, alternately, can comprise an adhesive material that encircles and sticks on to the rod 10 and can be removed and disposed of after use.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A fetal electrode device for introduction through the abdominal wall of a pregnant woman or animal for monitoring the fetal heart, comprising:
   a longitudinal electrode rod having a handle end and a pointed tip end with its handle end being adapted for electrically connecting to monitoring equipment; and
   an electrode tip portion at said pointed tip end of said electrode rod adapted to cut and penetrate through said abdominal wall, said longitudinal electrode rod being electrically insulated and having a length sufficient to extend through the abdominal section and uterine wall, and said electrode tip portion having an extension means from said rod for hooking said tip portion on to said fetus and thereby pick up electric signals therefrom.

2. A fetal electrode device as recited in claim 1, further comprising a protective shroud for sealing the area around said rod where it enters said abdominal wall.

3. A fetal electrode device as recited in claim 2 wherein said protective shroud encircles said electrode rod and is attached at one end to said handle end, the other end of said protective shroud including adhesive means for attaching said shroud to the abdominal skin in the area around said electrode rod, whereby sanitary conditions can be maintained during fetal monitoring.

4. A fetal electrode device as recited in claim 3 wherein said adhesive means includes a removable protective strip for adhesive material.

5. A fetal electrode device as recited in claim 3, wherein said adhesive means includes a ring of adhesive material attached at the end of the said shroud, with removable cover strip on said adhesive ring.

6. A fetal electrode device as recited in claim 1, wherein said electrode tip portion includes a helical electrode needle extension at the end of said longitudinal electrode rod, said helical extension including said pointed tip at its end such that the helical electrode needle extension will penetrate through said abdominal wall as said electrode rod is rotated and said helical tip portion will hook on to said fetus.

7. A fetal electrode device as recited in claim 1 wherein said electrode portion includes a straight tip portion with a cutting edge terminating in a pointed end, the back of said cutting edge having a small hook portion for holding the tip in place on the fetus skin, whereby said electrode tip portion will penetrate through said abdominal section as said rod is pushed into said abdominal wall.

8. A fetal electrode device as recited in claim 1 further comprising a protective covering material attached around said electrode rod and adhering to said abdominal skin whereby sanitary conditions are maintained in the area of the abdominal opening.

9. A fetal electrode device as recited in claim 1 wherein said longitudinal electrode rod is hollow to permit fluid medication to be injected through said hollow rod and its pointed tip end into said fetus.

10. A fetal electrode device for introduction through the abdominal wall of a pregnant woman or animal for monitoring the fetal heart, comprising:

a longitudinal electrode rod having a handle end and a pointed tip end with its handle and being adapted for electrically connecting to monitoring equipment;

an electrode tip portion at said pointed tip end of said electrode rod adapted to cut and penetrate through said abdominal wall, said longitudinal electrode rod being electrically insulated and having a length sufficient to extend through the abdominal section and uterine wall, and said electrode tip portion having an extension means from said rod for hooking said tip portion on to said fetus and thereby pick up electric signals therefrom; and a protective shroud which encircles said electrode rod and is attached at one end to said handle end, the other end of said protective shroud including adhesive means for attaching said shroud to the abdominal skin in the area around said electrode rod, whereby sanitary conditions can be maintained during fetal monitoring.

11. A fetal electrode for introduction through the abdominal wall of a pregnant woman or animal for monitoring the fetal heart, comprising a longitudinal electrode rod having at one end a handle means for rotating said shaft, said electrode rod having an insulating layer thereon and being adapted to electrically connect to monitoring equipment; and a helical electrode tip portion connected to the other end of said electrode rod as an extension therefrom and pointed to penetrate through the abdominal wall as said rod is rotated, said electrode rod having a length sufficient to extend through the abdominal section and uterine wall such that said electrode tip portion can hook onto said fetus and thereby pick up electric signals of the fetus.

* * * * *